United States Patent
Kaiser et al.

(10) Patent No.: US 8,823,526 B2
(45) Date of Patent: Sep. 2, 2014

(54) METHOD OF ASSESSING HUMAN FALL RISK USING MOBILE SYSTEMS

(75) Inventors: William J. Kaiser, Los Angeles, CA (US); Majid Sarrafzadeh, Anaheim Hills, CA (US); Hyduke Noshadi, Northridge, CA (US); Shaun S. Ahmadian, Rolling Hills Estates, CA (US); Hagop Hagopian, Glendale, CA (US); Navid Amini, Los Angeles, CA (US); Mars Lan, Los Angeles, CA (US); Jonathan S. Woodbridge, Los Angeles, CA (US); Wenyao Xu, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 275 days.

(21) Appl. No.: 13/378,937

(22) PCT Filed: Jun. 29, 2010

(86) PCT No.: PCT/US2010/040431
§ 371 (c)(1),
(2), (4) Date: Dec. 16, 2011

(87) PCT Pub. No.: WO2011/002788
PCT Pub. Date: Jan. 6, 2011

(65) Prior Publication Data
US 2012/0092169 A1 Apr. 19, 2012

Related U.S. Application Data (60) Provisional application No. 61/222,900, filed on Jul. 2, 2009.

(51) Int. Cl.
| | | |
|---|---|---|
| G08B 23/00 | (2006.01) |
| A61B 5/11 | (2006.01) |
| A61B 5/103 | (2006.01) |
| A61B 5/00 | (2006.01) |
| A61H 1/00 | (2006.01) |
| A63B 71/00 | (2006.01) |

(52) U.S. Cl.
CPC ......... *A61B 5/1038* (2013.01); *A61B 2562/046* (2013.01); *A61B 5/1117* (2013.01); *A61B 5/1116* (2013.01); *A61B 5/112* (2013.01); *A61B 5/6807* (2013.01); *A61B 5/7246* (2013.01); *A61B 5/7275* (2013.01)
USPC ........ 340/573.1; 600/587; 600/592; 600/595; 73/172; 601/34; 482/9

(58) Field of Classification Search
USPC .................. 340/573.1; 600/587, 595; 73/172
See application file for complete search history.

(56) References Cited

U.S. PATENT DOCUMENTS

| 5,209,240 A | 5/1993 | Jain et al. |
| 2006/0195050 A1 | 8/2006 | Alwan et al. |

(Continued)

FOREIGN PATENT DOCUMENTS

| KR | 10-0873495 | 12/2008 |
| KR | 10-0894895 | 4/2009 |

OTHER PUBLICATIONS

PCT International Search Report and Written Opinion, International Application No. PCT/US2010/040431, filed Jun. 29, 2010, Korean Intellectual Property Office, Feb. 8, 2011, 6 pages.

(Continued)

*Primary Examiner* — Jack K Wang
(74) *Attorney, Agent, or Firm* — Foley & Lardner LLP; Cliff Z. Liu; Angela D. Murch (57) ABSTRACT

A method for determining the motive instability of an individual using foot pressure, foot speed and foot direction data collected from sensors on shoes. The sensed data is used to determine the minimum number and the placement of pressure sensors in the shoe. The data from the sensors is processed to extract spatial and temporal parameters as desired. The data is grouped into segments based on a segmentation rule. The trend in each segment is determined. The variability of the trend in each segment is determined. The risk of fall is computed on the basis of the trend and variance. The computation is adjustable by emphasizing certain parameters in order to tailor the instability assessment to a specific individual.

19 Claims, 6 Drawing Sheets

(56) References Cited

U.S. PATENT DOCUMENTS

| | | | |
|---|---|---|---|
| 2006/0282021 A1 | 12/2006 | DeVaul et al. | |
| 2008/0133277 A1 | 6/2008 | Jang et al. | |
| 2008/0306410 A1* | 12/2008 | Kalpaxis et al. | 600/592 |
| 2009/0216156 A1* | 8/2009 | Lengsfeld et al. | 600/595 |
| 2011/0021320 A1* | 1/2011 | Lenhardt | 482/9 |
| 2011/0166488 A1* | 7/2011 | Miyake | 601/34 |

OTHER PUBLICATIONS

H. Noshadi et al., "HERMES Mobile Balance and Instability Assessment System", Computer Science Dept., UCLA, 6 pages.

H. Noshida, "Hermes: Mobile Balance and Fall Risk Assessment and Prevention System", IEEE Transactions on Information Technology in Biomedicine, Oct. 2008, 12 pages.

\* cited by examiner

METHOD OF ASSESSING HUMAN FALL RISK USING MOBILE SYSTEMS

CROSS-REFERENCE TO RELATED APPLICATIONS

This application claims the benefit of provisional application Ser. No. 61/222,900 filed Jul. 2, 2009 for Methods To Assess Human Fall Risk By Monitoring Balance Abnormality Using Mobile Pressure Based Systems, the entire disclosure thereof being incorporated herein by reference.

BACKGROUND OF THE INVENTION

1. Field of the Invention

The present invention relates generally to improvements in sensor systems for humans utilized to aid in medical diagnoses or provide assessment of physical conditions, and more particularly, pertains to assessing human instability and balance.

2. Description of Related Art

Fall related injuries are a growing challenge to healthcare systems. The cost of caring for individuals injured by falls for just those in the age group 65 and older is in the multiple billions of dollars annually.

Currently, healthcare systems do not have the capability to continuously monitor an individual's instability and fall risk outside of a hospital setting. Regular doctor visits which can provide personal assessment by the doctor as to an individual's mode of instability are helpful. However, the number of such visits required to be effective, amounts to excessive cost.

Currently, there are several methods used by physicians and geriatric experts for assessing instability and measuring imbalance of an individual. The first method involves the use of clinical tests that rely mainly on the trained eyes of a physician for evaluation and diagnosis. The second method is the use of expensive motion capture equipment in motion laboratories, along with pressure based devices. A third method involves the use of wearable mobile sensor platforms for balance and gait analysis, and for analysis of foot ulcers and fitness.

All these systems lack quantitative and reproducible measures, such as those acquired through an electronic device, or are limited to a controlled environment, such as a laboratory, and only support short duration examinations. Even the more recent mobile alternatives lack data and modeling techniques to properly assess instability and its progression.

The method of the present invention, however, which is based on the premises that gait variability can be an effective measure of fall risk overcomes these shortcomings of the prior systems.

SUMMARY OF THE INVENTION

A method for optimizing pressure sensor placement for a specific individual collects foot pressure data, and correlates the data into clusters. The clusters are tested for variability to determine which sensors contribute most to the data for a particular individual. The number of sensors can be reduced as desired. Sensed foot pressure, foot space and foot direction data is used to determine the fall risk for a particular individual. The sensed data is processed to extract spatial and temporal parameters. The data is grouped into segments, based on predetermined selector rules. The trends for the parameters in each segment is compiled. The variability of each parameter with respect to the trend in each segment is determined. The risk of a fall is computed for each segment on the basis of the variance of the temporal and spatiotemporal parameters in that segment. Certain parameters may be emphasized in order to track the instability assessment of a specific individual.

BRIEF DESCRIPTION OF THE DRAWINGS

The exact nature of this invention, as well as the objects and advantages thereof, will become readily apparent from consideration of the following specification in conjunction with the accompanying drawings, in which like reference numerals designate like parts throughout the figures thereof and wherein.

DETAILED DESCRIPTION OF THE PREFERRED EMBODIMENTS

Figure 1:
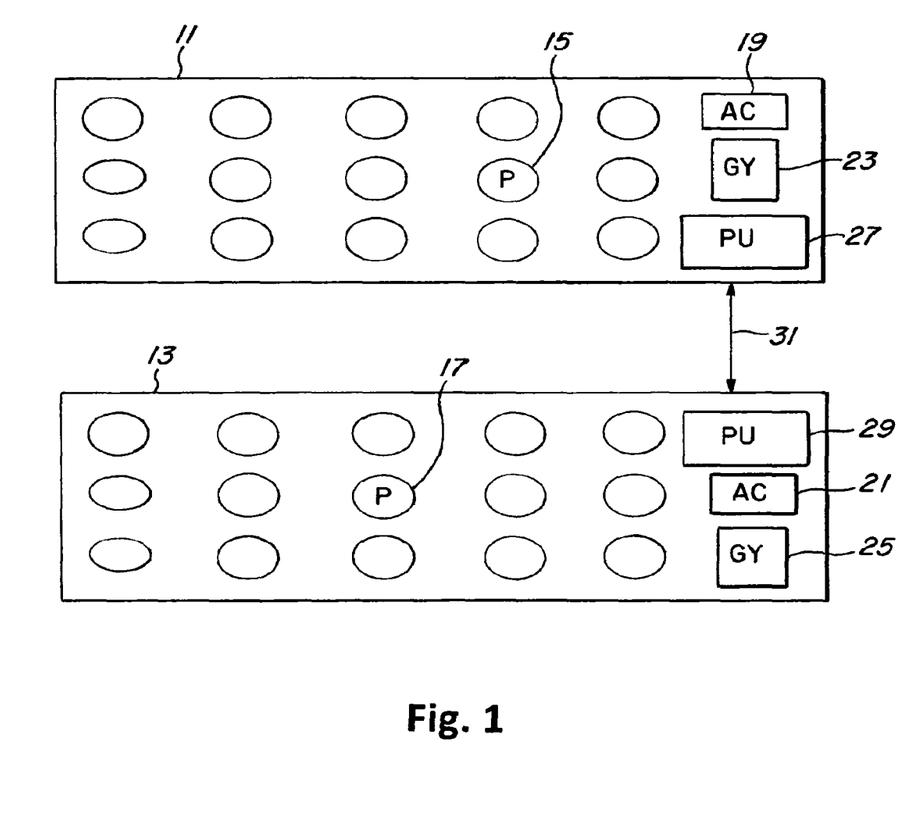
FIG. 1 is a block diagram illustration of insoles containing sensors.

FIG. 1 generally illustrates a right shoe 11 and a left shoe 13, and more specifically the sole or insole of a shoe which contains a plurality of pressure sensors 15, 17. The pressure sensors may be all of the same construction or of different construction, as is well known in the art. The location and size of the pressure sensors may vary depending upon the specific application for which the system is designed. The shoe also may have accelerometers 19, 21. The number of accelerometers, and their location in the shoe is also influenced by a particular application or system within which the sensors are used. The soles of the shoes may also contain gyroscopes 23, 25. The position of the gyroscopes is influenced by the particular application of the system. The gyroscopes and accelerometers may be embedded inside the insole of a shoe, or can be located outside of the insole, but with physical attachment to the insole by wires. Alternatively, the accelerometers and gyroscopes may be attached to the foot or the shoe.

The shoe may also contain a processing unit 27, 29 which may be located in the shoe or in the insole.

The location of the sensors 15, 17 in the insole of the shoe, for example, would preferably cover the entire surface of a foot resting on the insole. It is contemplated that an algorithm located in the local processing unit 27, 29, would decide whether to read or transmit from a particular sensor. The algorithm is designed to verify the values of adjacent sensors or detect incorrect sensor readings. The data collected from the accelerometer and gyro, as well as the aggregate values from each sensor, is utilized to identify possible incorrect sensor readings.

The processor units 27 and 29 in the respective right and left shoes are designed to talk to each other, add extra information, or readjust their packet numbers in order to synchronize the packets of information being sent from the left and right shoe. Alternatively, the data packets may be synchronized periodically at the receiving device.

Figure 2:
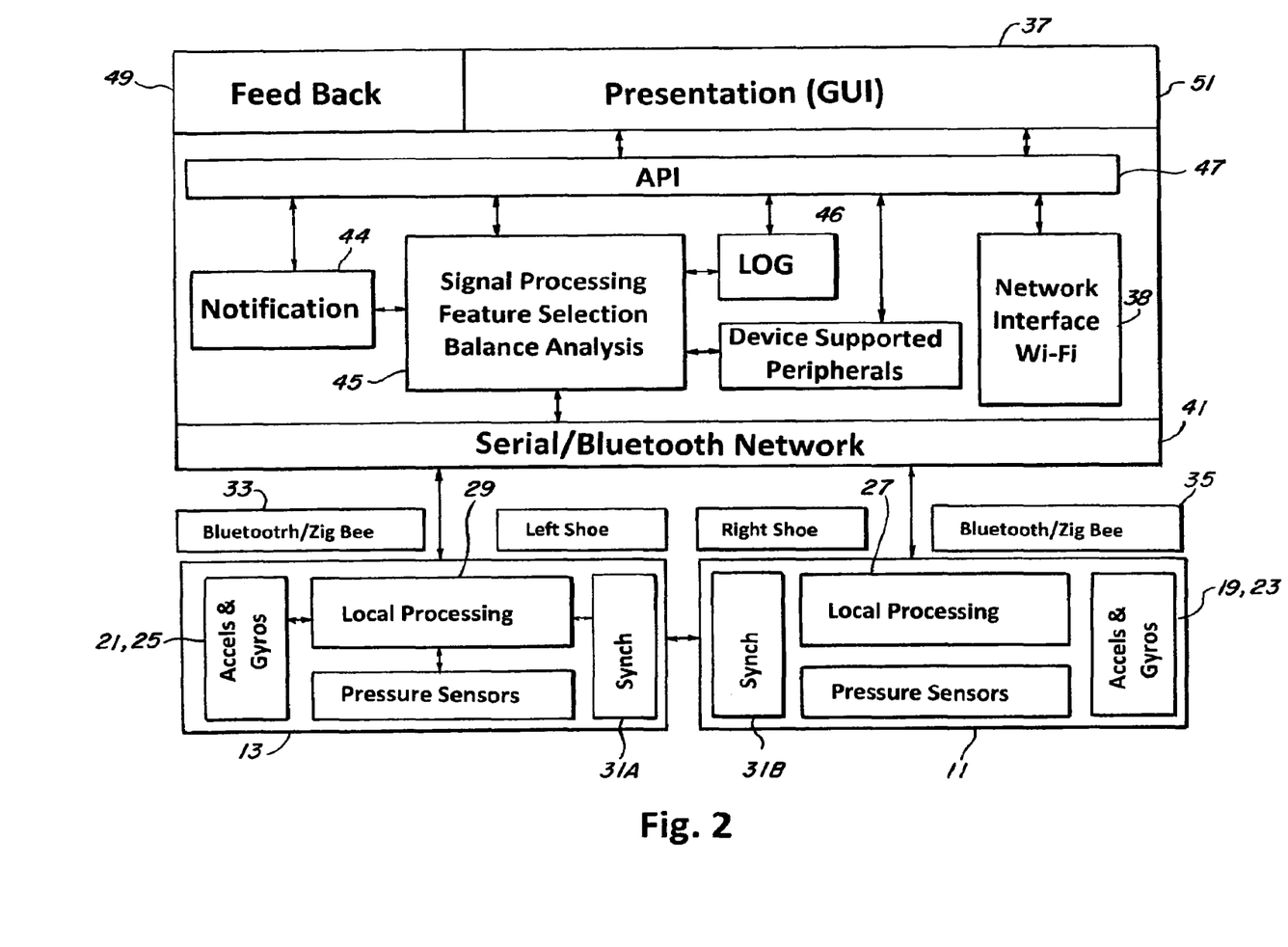
FIG. 2 is a block diagram of a system for practicing a method of the invention.

FIG. 2 illustrates a system in which the method of the present invention is practiced. The local processing units 27 and 29 that may be embedded inside the shoe, is responsible for data acquisition, preliminary data and signal analysis, time synchronization between the two shoes 11 and 13 of the data transferred to a personalized device or other site. The data, such as the sensor data collected by the local processing units 27, 29 at the shoe, are transferred to a personalized device or other analysis unit over radio or to Bluetooth® networks, which are well known in the art. The pressure sensor values are collected at appropriate time intervals. The sensor data collected in this manner can be streamed to a variety of devices as long as they are Bluetooth® enabled.

The system 37 which communicates with the left and right shoes 27, 29 by way of Bluetooth® devices 33, 35 or by radio interface, effectively has three layers: A network interface 41, processing 45, and a presentation unit 51. The processing segment 45 is responsible for logging streamed data, signal processing, and providing an API 47 to each of the components. The processing unit 45 performs different signal processing such as filtering, feature selection, and classification, to convert a raw signal into a meaningful chain of data which can then be interpreted, in this particular case an instability assessment. The logging module 46 stores received data from each sensor through the network interface 41. The logged data is then used for a variety of purposes, such as displaying activity on the graphical user interface 51. The graphical user interface 51 displays in real time, normalized data streams from each sensor along with accelerometer readings in separate plots for each sensor type. A notification unit 44 is triggered by events that occur in the processing unit 45, which can be an indication of an emergency in an abnormal situation, or any event which requires attention. The notification unit 44 is responsible for propagating the detected abnormality to the user by the user interface API 47 and various other mediums, such as e-mail and phone calls.

A specific arrangement for the sensing portion of the system which the inventors have utilized consists of an onboard three axis accelerometer and three axis gyroscope in each shoe, along with seven pressure sensors integrated within the shoe's insole. Each shoe is identically arranged. The gyroscope and accelerometer are mounted in the shoe's heel so that an axis of the gyroscope and accelerometer is aligned with the individual's body. Preferably all sensor data is collected with a 16-bit ADC.

Signal processing is accomplished by the remotely located processing system 37. Generally, signal conditioning, filtering and segmentation is part of pre-processing. The processing stage performs temporal, spatiotemporal and consistency analysis, extracting spatiotemporal and consistently features from the measured data in order to determine fall risk instability.

Figure 3:
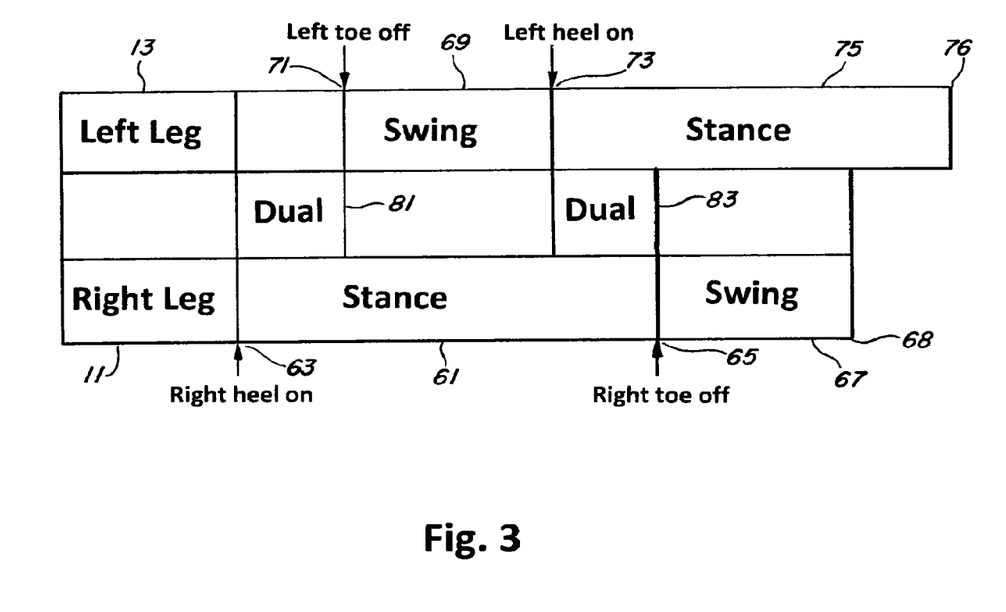
FIG. 3 is a diagrammatic illustration of foot movement by an individual.
Figure 4:
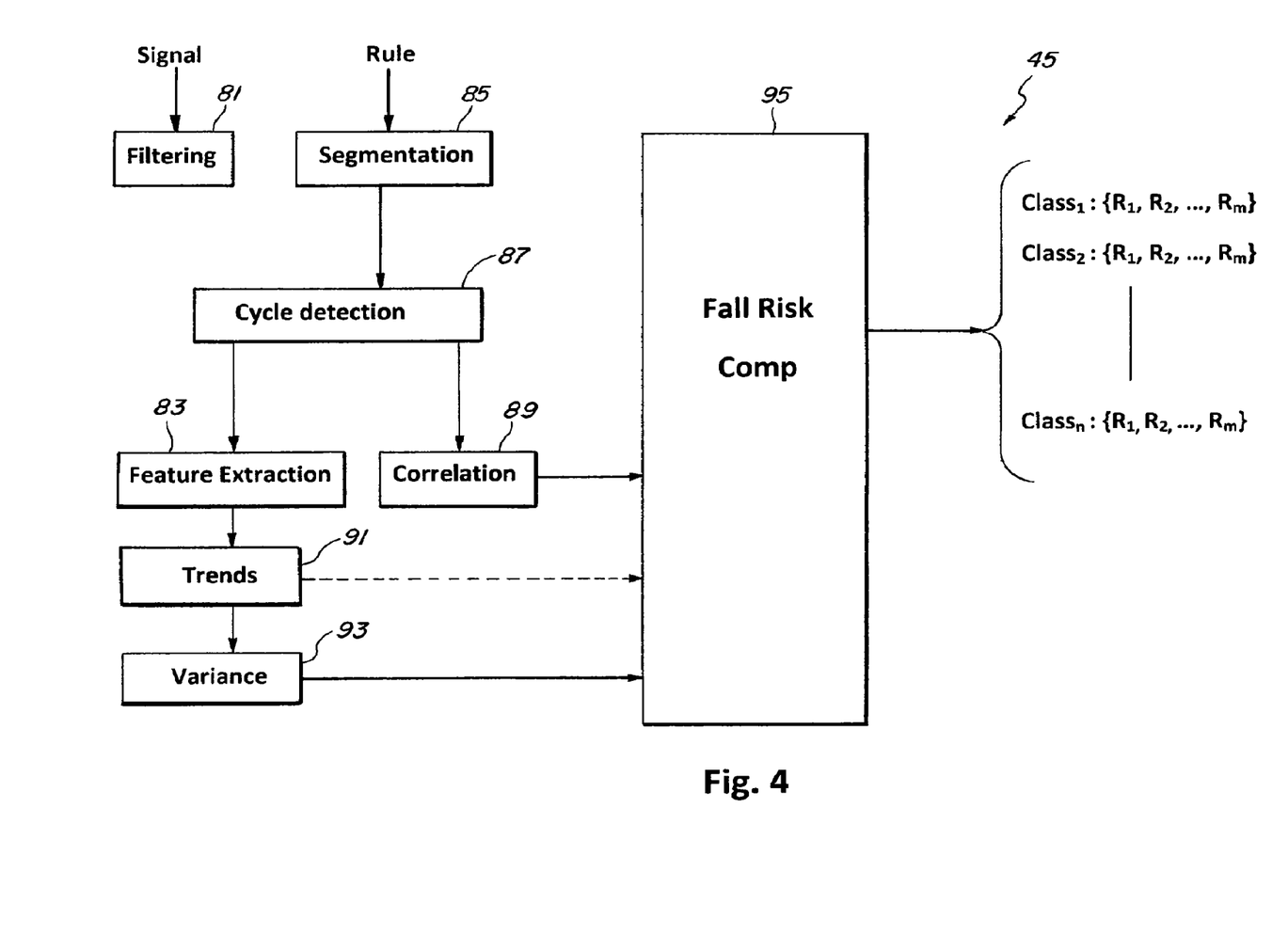
FIG. 4 is a block diagram illustrating a method of fall risk assessment.

The spatial and the temporal parameters that are extracted from the signals coming from the sensors in the shoes 11, 13 include step length, step time, cadence, stride length, gait speed, stance-to-swing ratio, dual stance and pressure correlation. Step length is the distance from a point of contact with the ground of one foot to the following occurrence at the same point of contact of the other foot. This can generally be thought of as the distance one foot moves forward in front of the other. Step time is the time taken for each step. Cadence is the number of steps taken per second. Stride length is the distance between successive points of initial contact by the same foot. Stride length consists of two step lengths, left and right. Gait speed is the product of stride length and cadence. Stance-to-swing ratio is a ratio of the stance time to swing time. The stand phase is the time from heel contact to toe off, such as stance 61 for the right leg 11, and stance 75 for the right leg 13, illustrated in FIG. 3. The stance phase 61 for the right leg 11 is the time between the right heel contact 63 to the right toe off 65. The left leg 13 stance phase 75 is the time between the left heel contact 73 to the left toe off 76. The swing phase 69, 67 is the time between toe off and heel contact, as shown in FIG. 3. The swing phase 69 for the left leg 13 is the time between left toe off 71 and left heel on 73. The swing phase 67 for the right leg 11 is the time between right toe off 65, right heel on 68. Normal ambulation contains 60% of a stance phase 75, 61 and 40% of a swing phase 69, 67, as illustrated in FIG. 4. Dual stance is the time both feet are in contact with the ground. Pressure correlation is the correlation of the pressure rendered in each step with the previous step.

In addition to the above parameters, spatial and temporal features such as position of the heel during heel strike, center of pressure line, plantar pressure distribution during HC, MS, FFL and TO, force transition during gait cycle, and heel rotation during toe off may also be determined. The position of the heel during heel strike is the point on the heel touching the ground. The center of the pressure line is a measure of the average sensor lead on each line perpendicular to the heel-toe axis. Plantar pressure distribution is the percentage of pressure on each sensor in each of the four regions. Force transition during gait cycle is equivalent to transition of center of the mass. Heel rotation during toe off is the amount the heel rotates when the foot leaves the ground.

These features are only examples of features that may be used in an analysis. Additional features or parameters that are related to time, space and geography and are changing based on time, space and geography can be extracted from the data and is considered a feature the preferred embodiment of the present application.

FIG. 4 illustrates the method according to the preferred embodiment of determining a fall risk indication. Pre-processing steps involve signal filtering 81 and segmentation 85, based on the implemented segmentation rule. The segmentation rule is designed to characterize each segment into different classes. The segmentation rule is set by the person that has interest in the data. The segmentation rule effectively identifies the granularity of the analysis of the data. Some examples of the segmentation rules are, a fixed time interval, type of activity, i.e., walking or running, or a set of events triggered by external factors such as geographical location, which can be provided by a GPS device. Many other segmentation rules are possible.

The processing step extracts temporal parameters and spatial parameters from the pressure signal data. The extraction of left and right stance phase, left and right swing phase, and dual-support phase features, for example, is accomplished by processing a minimum of four signals which are mostly closely associated to the point of pressure for the toe and heel. The signals are discretized and sanitized input pressure signals that represent occurrences of pressure contact on and pressure contact off. Given these occurrences, we know exactly where the following occur: Right heel on, right toe off, left heel on and left toe off, for a single step cycle. These are the only events that need to be detected in order to generate all the temporal features. The temporal features are calculated as follows: Left/right stance phase is the time between the heel on and toe off Left/right swing phase is the time between toe off and heel on. Dual support is the time between right heel on and left heel off.

The spatial parameters are extracted from both the pressure and non-pressure data. The signals required from the pressure sensors are used to compute step consistency by computing the correlation of consecutive steps in real time. The signal readings from the accelerometer and gyroscope are used to compute the stride and step length using techniques well known in the prior art.

Step consistency is calculated in real time by computing the difference of two consecutive signals by taking the difference of their integral over time according to equation (1):

$$C = 1/k \sum_{i=S-k}^{S-1} \left( \int_{bs_{i+1}}^{es_{i+1}} P(t)dt - \int_{bs_i}^{es_i} P(t)dt \right) \quad (1)$$

where k is the operation window, S is the maximum number of steps taken, es and bs are the beginning and end point of the step and P(x) is the function of recorded sensor value over time. Preferably the median difference is tracked over a window of the five most recent steps (K=5).

Once the data is segmented according to the segmentation rules, then the interest points, which are used for feature extraction, are detected in each cycle 87. A correlation of neighboring cycles in the same segment of each signal received from pressure based and non-pressure based sensors is computed 89. The goal here is to quantify the similarity, harmony and cycle consistency. For each cycle a correlation relation is generated which is relative to the previous cycle and the base line cycle of the same signal. The gradual shift of each extracted feature is computed over time. The gradual shift represents the change in an active subject, and is used as the baseline to measure the variability of the detected temporal and spatiotemporal features. Once the trends of the features are computed, the variability of each feature is calculated relative to the trend. The trends 91 and variances 93 are, along with the correlation 89, supplied to the fall risk assessment calculation.

The trend is defined as the true behavior or activity that is observable. It is important to distinguish between trend and variance. Trend is the true tendency of the variation. Variance is deviation of the data from the trend. To develop a trend for given data, a multi-pass interpolation with a pre-defined window is used to determine the relative average path.

Trend analysis is important as an accurate predictor of behavior. Accurate predictions of behavior of an individual at any given time is a key component in the instability analysis model.

The variance analysis 93 performed by the system follows the trend analysis 91. After the features are computed for each step cycle and trend functions computed for the signal in each segment, the variability of each feature using equation (2) is obtained:

$$Var_{feature_k} = \sqrt{1/n - 1 \sum_{i=t}^{t+k} (pi - \overline{p})^2} \quad (2)$$

where $p_i$ is the value of the features' variance relative to the trend as described in equation (3):

$$pi = s_i - \gamma(s_i) \quad (3)$$

where γ is the trend function that is constructed as specified.

If an individual is attempting to increase their speed, for example, but are having difficulty doing so consistently, that individual is generally at a higher risk of falling. That is why the variance analysis is important for determining instability. In general, a stronger variance in a feature implies a higher fall risk instability.

Once the trend and variability of each feature relative to trend is computed, the measure for instability can be established for each segment of input signal based on equation (4):

$$\text{Instability} = V_T + V_{ST} = \sum_{i=1}^{n} \alpha_i V_{\tau_i} + \sum_{j=1}^{m} \gamma j V \sigma_j \quad (4)$$

where $V_T$ and $V_{ST}$ are the variance of temporal and spatiotemporal parameters in a segment. Where $\tau_i$ is the variance of temporal feature i, and $\sigma_j$ is the variance of spatiotemporal feature j while $\alpha_i$ and $\gamma_j$ are the coefficients which indicate the importance of a particular feature. These coefficients are constrained by equation (5):

$$\sum_{i=1}^{n} \alpha_i + \sum_{j=1}^{m} \gamma j = 1 \quad (5)$$

The coefficients can be set by a physician or other expert to tailor the instability assessment to a particular individual.

Figure 5:
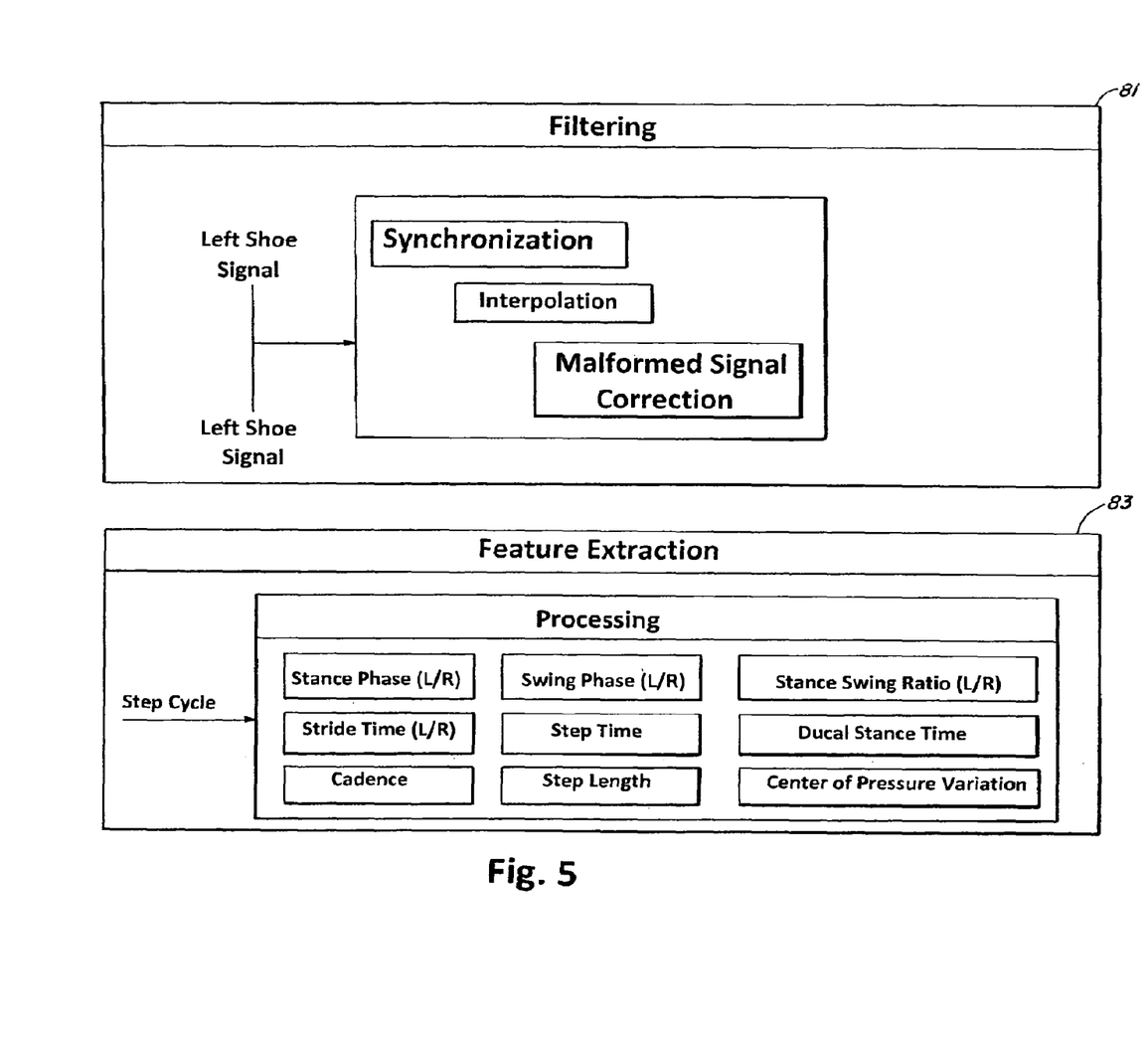
FIG. 5 is a diagrammatic illustration of the filtering process and feature extraction process used in the fall risk assessment method illustrated in FIG. 4.

FIG. 5 illustrates in greater detail the pre-processing filtering stage 81 which performs synchronization, interpolation and malformed signal correction and the feature extraction function 83, which for each step cycle performs the feature computations indicated.

The performance of the above described method is optimized by sensor selection. Sensor selection refers to selecting a subset of the available sensors and only monitoring the data from this subset. Sampling each sensor, storing the data from all the sensors and transmitting all the data requires considerable power and memory resources. These resources are hard to come by in a lower power mobile system such as contemplated by the present invention.

Sensor selection or placement must be customized for the individual user. To find the structure of the underlying data that is most significant for the individual user, clustering may be used. Clustering requires a similarity measure to group the data points of interest. This is accomplished by correlation. Specifically, a graph-theoretic approach known as divisive (top down) clustering is used to build a hierarchical structure which is then pruned based on empirical measurements.

Figure 6:
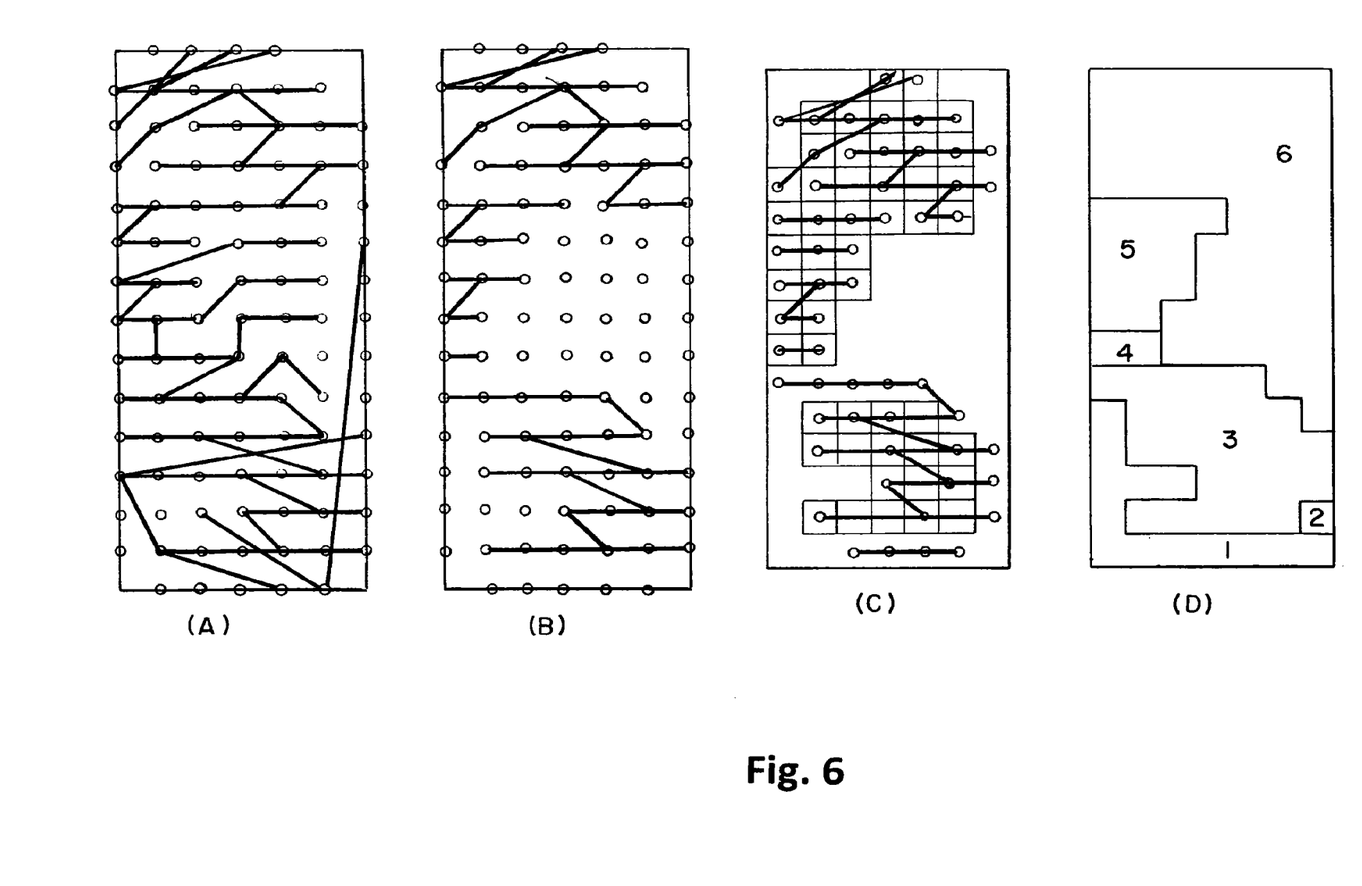
FIG. 6 is a diagrammatic illustration of the sensor selection process that can be used in the present invention.

The first step is to build a similarity graph where nodes are sensors and edges are the correlations between sensors. From this similarity graph, one can derive a minimal spanning tree such as illustrated in FIG. 6A. The minimal spanning tree is used as the baseline structure for divisive pruning and clustering. Due to the nature of spanning trees, they will have a combination of strong and weak links. To remove weak links, an empirically derived threshold is used to obtain a pruned tree similar to FIG. 6B. To determine if the clusters formed as a result of such pruning contributes significantly to the overall signal, a second measure called variability is used. FIG. 6C illustrates the pruned spanning tree of FIG. 6B overlaid by a variance map, where the lighter colors indicate greater variability in the sensing channel. As can be seen, most of the clusters fall within regions of high variability while smaller clusters fall in regions which contribute minimally to the overall signal. Using the variability map as a guide, unnecessary clusters are pruned to derive the final set of clusters, shown in FIG. 6D.

The spanning tree derived from the similarity graph, provides insight into the structure of the underlying data. FIG. 6A shows the full minimum spanning tree. Some noticeable features are the horizontal and vertical connections. The horizontal connections indicate temporal consistency, meaning the shift of pressure from the back (heels) to the front (toes) is highly synchronized horizontally. The existence of vertical connections indicate spatial consistency as a result of a flatter application of pressure. Many other factors influence correlation of the signals. We are only showing the higher level inferences that can be derived from quantitative measures such as correlation.

Clustering of the underlying data is application dependent. The needs of the physician or analyst will dictate the number of sensors needed to output the desired statistics. In order to output the statistics of interest, in order to determine the correct number of clusters for a particular application, a loss function criteria may be used as the average intra-cluster error, and then empirically derive the cluster count, which minimizes the criteria function.

What is claimed is:

1. A method for determining fall risk instability for a specific individual comprising: measuring data from sensors located in the shoes of an individual in motion; analyzing the measured data to determine trends in the data, the analyzing including, for a predetermined number of step cycles, correlating sensor data between each two consecutive ones of the step cycles; and using results of the correlations, determining a trend of a feature of interest; analyzing the measured data to determine variances in the trends; and determining fall risk instability based on the determined variances.

2. The method of claim 1 further comprising generating a warning signal when the determined fall risk instability exceeds a predetermined threshold.

3. The method of claim 1 wherein the data from the sensors, located in the shoes of the individual in motion provide data to determine the parameter step length, dual stance time, cadence, time for each taken step, gait, stride length, stance-to-swing phase ratio, pressure correlation, center line of pressure, or planar pressure distribution.

4. The method of claim 3 wherein each determined parameter is assigned a weighting factor based on the individual characteristics of the individual, or his environment.

5. The method of claim 1, further comprising segmenting the measured data into classes according to a predetermined rule.

6. The method of claim 5 wherein the predetermined rule for segmentation may be a fixed time interval, type of activity, or geographical location.

7. The method of claim 1 wherein the measuring the data comprises extracting temporal features and spatiotemporal features from the measured data.

8. The method of claim 7 wherein the determining the trends comprises determining trends in the temporal features and spatiotemporal features.

9. The method of claim 8 where the determining the variances comprises determining variances in the trends of the temporal features and spatiotemporal features.

10. The method of claim 9 where the determining the fall risk instability comprises analyzing the variances in the trends of the temporal features and spatiotemporal features.

11. A method, comprising:
receiving sensor data from sensors in a shoe;
from the sensor data, detecting the beginning and end of each of a plurality of step cycles;
for a predetermined number of step cycles, correlating sensor data between each two consecutive ones of the step cycles;
using results of the correlations, determining a trend of a feature of interest;
using the results of the correlations, determining a variation from the trend; and
from the trend and variation, calculating a risk of instability.

12. The method of claim 11, wherein the sensor data includes temporal and spatial data.

13. The method of claim 11, wherein determining the trend includes performing a multi-pass interpolation using a predefined window to determine a relative average path.

14. The method of claim 11, wherein calculating a risk of instability includes calculating a sum of a variance of temporal parameters and a sum of a variance of spatiotemporal parameters.

15. The method of claim 11, further comprising: identifying a subset of the sensors, wherein the identification of a sensor to include in the subset of the sensors is based on the relative influence of the sensor data from that sensor on the determination of the feature of interest.

16. The method of claim 15, wherein identifying the subset of the sensors includes using a clustering technique.

17. The method of claim 15, wherein receiving the sensor data includes receiving sensor data from the subset of the sensors and not receiving sensor data from sensors outside of the subset of the sensors.

18. The method of claim 11, wherein the sensor data is received through a wireless interface.

19. The method of claim 11, wherein the sensor data is received and processed in the shoe.

* * * * *